United States Patent
Hantke et al.

(10) Patent No.: US 9,028,876 B2
(45) Date of Patent: *May 12, 2015

(54) RATE-CONTROLLED PARTICLES

(75) Inventors: Thomas Hantke, Mannheim (DE);
Bettina Rehbock, Dannstadt (DE); Jörg Rosenberg, Ellerstadt (DE); Jörg Breitenbach, Mannheim (DE)

(73) Assignee: Janssen R&D Ireland, Little Island, Co. Cork (IE)

( * ) Notice: Subject to any disclaimer, the term of this patent is extended or adjusted under 35 U.S.C. 154(b) by 2 days.

This patent is subject to a terminal disclaimer.

(21) Appl. No.: 13/420,013

(22) Filed: Mar. 14, 2012

(65) Prior Publication Data

US 2012/0172364 A1 Jul. 5, 2012

Related U.S. Application Data

(60) Continuation of application No. 12/368,884, filed on Feb. 10, 2009, now abandoned, which is a division of application No. 10/088,400, filed as application No. PCT/EP00/09149 on Sep. 19, 2000, now abandoned.

(30) Foreign Application Priority Data

Sep. 24, 1999 (DE) .................................. 199 45 982

(51) Int. Cl.
| | | |
|---|---|---|
| *A61K 9/14* | (2006.01) | |
| *A61K 9/50* | (2006.01) | |
| *A61K 9/22* | (2006.01) | |
| *A61K 9/20* | (2006.01) | |
| *A61K 31/505* | (2006.01) | |
| *A61K 31/50* | (2006.01) | |
| *A61K 31/497* | (2006.01) | |
| *C07D 239/48* | (2006.01) | |
| *A61K 31/496* | (2006.01) | |
| *A61K 31/53* | (2006.01) | |
| *C07D 231/12* | (2006.01) | |
| *C07D 233/56* | (2006.01) | |
| *C07D 239/50* | (2006.01) | |
| *C07D 249/08* | (2006.01) | |
| *C07D 251/18* | (2006.01) | |
| *C07D 403/12* | (2006.01) | |
| *C07D 405/14* | (2006.01) | |
| *A61K 9/16* | (2006.01) | |

(52) U.S. Cl.
CPC ............ *C07D 239/48* (2013.01); *A61K 9/1635* (2013.01); *A61K 31/496* (2013.01); *A61K 31/505* (2013.01); *A61K 31/53* (2013.01); *C07D 231/12* (2013.01); *C07D 233/56* (2013.01); *C07D 239/50* (2013.01); *C07D 249/08* (2013.01); *C07D 251/18* (2013.01); *C07D 403/12* (2013.01); *C07D 405/14* (2013.01)

(58) Field of Classification Search
CPC .. A61K 31/496; A61K 31/505; A61K 9/1635
USPC .......... 424/400, 489, 464, 501, 468; 514/275, 514/252.01, 252.1
See application file for complete search history.

(56) References Cited

U.S. PATENT DOCUMENTS

| | | | |
|---|---|---|---|
| 4,801,460 A | 1/1989 | Goertz et al. ................. 424/465 |
| 4,917,900 A | 4/1990 | Jones et al. .................... 424/493 |
| 5,350,741 A | 9/1994 | Takada .............................. 514/3 |
| 5,456,923 A | 10/1995 | Nakamichi et al. ........... 424/489 |
| 5,876,760 A | 3/1999 | Sasatani et al. ............... 424/494 |
| 5,880,130 A | 3/1999 | Thomas ........................ 514/256 |
| 6,197,779 B1 | 3/2001 | Andries et al. ................. 514/272 |
| 6,878,717 B2 | 4/2005 | De Corte et al. .............. 514/269 |
| 7,037,917 B2 * | 5/2006 | De Corte et al. .............. 514/272 |
| 8,003,789 B2 * | 8/2011 | De Corte et al. .............. 544/321 |
| 8,530,665 B2 * | 9/2013 | Diseroad ....................... 546/339 |
| 2005/0288278 A1 | 12/2005 | De Corte et al. .............. 514/221 |
| 2008/0176880 A1 | 7/2008 | De Corte et al. .............. 514/275 |

FOREIGN PATENT DOCUMENTS

| | | |
|---|---|---|
| EP | 0 240 904 | 10/1987 |
| EP | 0 580 860 | 2/1994 |
| EP | 0 834 507 | 4/1998 |
| EP | 0 872 233 | 10/1998 |
| EP | 0 945 443 | 9/1999 |
| WO | WO 91/18887 | 12/1991 |
| WO | WO 96/13499 | 5/1996 |
| WO | WO 97/19065 | 5/1997 |
| WO | WO 98/41512 | 9/1998 |
| WO | WO 99/02523 | 1/1999 |
| WO | WO 99/50250 | 10/1999 |
| WO | WO 99/50256 | 10/1999 |
| WO | WO 00/27828 | 5/2000 |

* cited by examiner

*Primary Examiner* — Shengjun Wang
(74) *Attorney, Agent, or Firm* — Novak Druce Connolly Bove + Quigg LLP

(57) ABSTRACT

Rate-controlled particles, comprising compounds of the formula

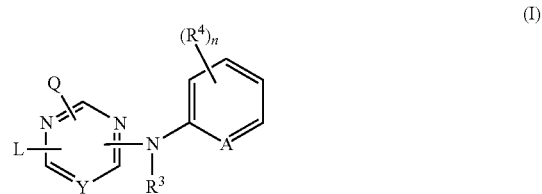

as a solid dispersion.

16 Claims, No Drawings

RATE-CONTROLLED PARTICLES

This is a Continuation application of application Ser. No. 12/368,884, filed on Feb. 10, 2009 now abandoned, which is a Divisional Application of application Ser. No. 10/088,400, filed on Jul. 22, 2002 now abandoned, which is a National Stage Application under 35 U.S.C. §371, of International Application No. PCT/EP 00/09149, filed on Sep. 19, 2000. The entire disclosure of each of the referenced applications is herewith incorporated by reference.

The present invention concerns pharmaceutical compositions in the form of rate-controlled particles, comprising compounds of the formula (I) to (VI)

(I) is an antiviral compound of formula

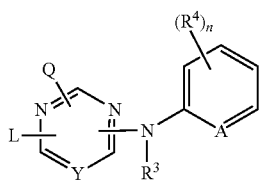

(I)

a N-oxide, a pharmaceutically acceptable addition salt or a stereochemically isomeric form thereof, wherein
Y is $CR^5$ or N;
A is CH, $CR^4$ or N;
n is 0, 1, 2, 3 or 4;
Q is $-NR^1R^2$ or when Y is $CR^5$ then Q may also be hydrogen;
$R^1$ and $R^2$ are each independently selected from hydrogen, hydroxy, $C_{1-12}$alkylcarbonyl, $C_{1-12}$alkyloxycarbonyl, aryl, amino, mono- or di($C_{1-12}$alkyl)-amino, mono- or di($C_{1-12}$alkyl)aminocarbonyl wherein each of the aforementioned $C_{1-12}$alkyl groups may optionally and each individually be substituted with one or two substituents each independently selected from hydroxy, $C_{2-6}$alkyloxy, hydroxy-$C_{1-6}$alkyloxy, carboxyl, $C_{1-6}$alkyloxycarbonyl, cyano, amino, imino, aminocarbonyl, aminocarbonylamino, mono- or di($C_{1-6}$alkyl)amino, aryl and Het; or
$R^1$ and $R^2$ taken together may form pyrrolidinyl, piperidinyl, morpholinyl, azido or mono- or di($C_{1-12}$alkyl)amino$C_{1-4}$-alkylidene;
$R^3$ is hydrogen, aryl, $C_{1-6}$alkylcarbonyl, $C_{1-6}$alkyloxy-carbonyl, $C_{1-6}$alkyl substituted with $C_{1-6}$alkyloxycarbonyl; and
each $R^4$ independently is hydroxy, halo, $C_{1-6}$alkyl, $C_{1-6}$alkyloxy, cyano, aminocarbonyl, nitro, amino, trihalomethyl, trihalo-methyloxy, or when Y is $CR^5$ then $R^4$ may also represent $C_{1-6}$alkyl substituted with cyano or aminocarbonyl;
$R^5$ is hydrogen or $C_{1-4}$alkyl;
L is $-X^1-R^6$ or $-X^2$-Alk-$R^7$ wherein
  $R^6$ and $R^7$ each independently are phenyl or phenyl substituted with one, two, three, four or five substituents each independently selected from halo, hydroxy, $C_{2-6}$alkyl, $C_{1-6}$alkyloxy, $C_{1-6}$alkylcarbonyl, $C_{1-6}$alkyloxycarbonyl, formyl, cyano, nitro, amino, and trifluoromethyl; or
  when Y is $CR^5$ then $R^6$ and $R^7$ may also be selected from phenyl substituted with one, two, three, four or five substituents each independently selected from aminocarbonyl, trihalomethyloxy and trihalomethyl; or
  when Y is N then $R^6$ and $R^7$ may also be selected from indanyl or indolyl, each of said indanyl or indolyl may be substituted with one, two, three, four or five substituents each independently selected from halo, hydroxy, $C_{1-6}$alkyl, $C_{1-6}$alkyloxy, $C_{1-6}$alkylcarbonyl, $C_{1-6}$alkyloxycarbonyl, formyl, cyano, nitro, amino, and trifluoromethyl;

$X^1$ and $X^2$ are each independently $-NR^3-$, $-NH-NH-$, $-N=N-$, $-O-$, $-S-$, $-S(=O)-$ or $-S(=O)_2-$;
Alk is $C_{1-4}$alkanediyl; or
when Y is $CR^5$ then L may also be selected from $C_{1-10}$alkyl, $C_{3-10}$alkenyl, $C_{3-10}$alkynyl, $C_{3-7}$cycloalkyl, or $C_{1-10}$alkyl substituted with one or two substituents independently selected from $C_{3-7}$cycloalkyl, indanyl, indolyl and phenyl, wherein said phenyl, indanyl and indolyl may be substituted with one, two, three, four or where possible five substituents each independently selected from halo, hydroxy, $C_{1-6}$alkyl, $C_{1-6}$alkyloxy, cyano, aminocarbonyl, $C_{1-6}$alkyloxy-carbonyl, formyl, nitro, amino, trihalomethyl, trihalomethyl-oxy and $C_{1-6}$alkylcarbonyl;
aryl is phenyl or phenyl substituted with one, two, three, four or five substituents each independently selected from halo, $C_{1-6}$alkyl, $C_{1-6}$alkyloxy, cyano, nitro and trifluoromethyl;
Het is an aliphatic or aromatic heterocyclic radical; said aliphatic heterocyclic radical is selected from pyrrolidinyl, piperidinyl, homopiperidinyl, piperazinyl, morpholinyl, tetrahydrofuranyl and tetrahydrothienyl wherein each of said aliphatic heterocyclic radical may optionally be substituted with an oxo group; and said aromatic heterocyclic radical is selected from pyrrolyl, furanyl, thienyl, pyridyl, pyrimidinyl, pyrazinyl and pyridazinyl wherein each of said aromatic heterocyclic radical may optionally be substituted with hydroxy.

REFERENCE TO JOINT RESEARCH AGREEMENT

This application arises under an agreement between Janssen Pharmaceutica N.V. and Knoll A.G.

The compounds of formula (I) can be prepared according to the methods described in the patent applications with application number PCT/EP99/02043 and PCT/EP99/02044.

(II) is an antiviral compound of formula

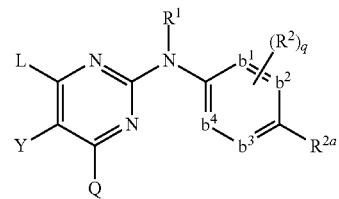

(II)

the N-oxides, the pharmaceutically acceptable addition salts, quaternary amines and the stereochemically isomeric forms thereof, wherein
$-b^1=b^2-C(R^{2a})=b^3-b^4=$ represents a bivalent radical of formula $$-CH=CH-C(R^{2a})=CH-CH= \quad (b-1);$$

$$-N=CH-C(R^{2a})=CH-CH= \quad (b-2);$$

$$-CH=N-C(R^{2a})=CH-CH= \quad (b-3);$$

$$-N=CH-C(R^{2a})=N-CH= \quad (b-4);$$

$$-N=CH-C(R^{2a})=CH-N= \quad (b-5);$$

$$-CH=N-C(R^{2a})=N-CH= \quad (b-6);$$

$$-N=N-C(R^{2a})=CH-CH= \quad (b-7);$$

q is 0, 1, 2; or where possible q is 3 or 4;

$R^1$ is hydrogen, aryl, formyl, $C_{1-6}$alkylcarbonyl, $C_{1-6}$alkyl, $C_{1-6}$alkyloxycarbonyl, $C_{1-6}$alkyl substituted with formyl, $C_{1-6}$alkylcarbonyl, $C_{1-6}$alkyloxycarbonyl;

$R^{2a}$ is cyano, aminocarbonyl, mono- or di(methyl)aminocarbonyl, $C_{1-6}$alkyl substituted with cyano, aminocarbonyl or mono- or di(methyl)aminocarbonyl, $C_{2-6}$alkenyl substituted with cyano, or $C_{2-6}$alkynyl substituted with cyano;

each $R^2$ independently is hydroxy, halo, $C_{1-6}$alkyl optionally substituted with cyano or —C(=O)$R^6$, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, —S(=O)$_p$$R^6$, —NH—S(=O)$_p$$R^6$, —C(=O)$R^6$, —NHC(=O)H, —C(=O)NHNH$_2$, —NHC(=O)$R^6$, —C(=NH)$R^6$ or a radical of formula

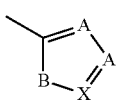

(c)

wherein each A independently is N, CH or CR$^6$;

B is NH, O, S or NR$^6$;

p is 1 or 2; and $R^6$ is methyl, amino, mono- or dimethylamino or polyhalomethyl;

L is $C_{1-10}$ alkyl, $C_{2-10}$alkenyl, $C_{2-10}$alkynyl, $C_{3-7}$cycloalkyl, whereby each of said aliphatic group may be substituted with one or two substituents independently selected from $C_{3-7}$cycloalkyl, indolyl or isoindolyl, each optionally substituted with one, two, three or four substituents each independently selected from halo, $C_{1-6}$alkyl, hydroxy, $C_{1-6}$alkyloxy, cyano, aminocarbonyl, nitro, amino, polyhalomethyl, poly-halomethyloxy and $C_{1-6}$alkylcarbonyl, phenyl, pyridinyl, pyrimidinyl, pyrazinyl or pyridazinyl, wherein each of said aromatic rings may optionally be substituted with one, two, three, four or five substituents each independently selected from the substituents defined in $R^2$; or L is —X—$R^3$ wherein $R^3$ is phenyl, pyridinyl, pyrimidinyl, pyrazinyl or pyridazinyl, wherein each of said aromatic rings may optionally be substituted with one, two, three, four or five substituents each independently selected from the substituents defined in $R^2$; and X is —NR$^1$—, —NH—NH—, —N=N—, —O—, —C(=O)—, —CHOH—, —S—, —S(=O)— or —S(=O)$_2$—;

Q represents hydrogen, $C_{1-6}$alkyl, halo, polyhalo$C_{1-6}$alkyl or —NR$^4$R$^5$; and $R^4$ and $R^5$ are each independently selected from hydrogen, hydroxy, $C_{1-12}$alkyl, $C_{1-12}$alkyloxy, $C_{1-12}$alkylcarbonyl, $C_{1-12}$alkyloxy-carbonyl, aryl, amino, mono- or di($C_{1-12}$alkyl)amino, mono- or di($C_{1-12}$alkyl)aminocarbonyl wherein each of the aforementioned $C_{1-12}$alkyl groups may optionally and each individually be substituted with one or two substituents each independently selected from hydroxy, $C_{1-6}$ alkyloxy, hydroxy$C_{1-6}$alkyloxy, carboxyl, $C_{1-6}$alkyloxycarbonyl, cyano, amino, imino, mono- or di($C_{1-6}$alkyl)amino, polyhalomethyl, polyhalomethyloxy, poly-halomethylthio, —S(=O)$_p$R$^6$, —NH—S(=O)$_p$R$^6$, —C(=O)R$^6$, —NHC(=O)H, —C(=O)NHNH$_2$, —NHC(=O)R$^6$, —C(=NH)R$^6$, aryl and Het; or $R^4$ and $R^5$ taken together may form pyrrolidinyl, piperidinyl, morpholinyl, azido or mono- or di($C_{1-12}$alkyl)amino$C_{1-4}$alkylidene;

Y represents hydroxy, halo, $C_{3-7}$cycloalkyl, $C_{2-6}$alkenyl optionally substituted with one or more halogen atoms, $C_{2-6}$alkynyl optionally substituted with one or more halogen atoms, $C_{1-6}$alkyl substituted with cyano or —C(=O)R$^6$, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, poly-halomethylthio, —S(=O)$_p$R$^6$, —NH—S(=O)$_p$R$^6$, —C(=O)R$^6$, —NHC(=O)H, —C(=O)NHNH$_2$, —NHC(=O)R$^6$, —C(=NH)R$^6$ or aryl;

aryl is phenyl or phenyl substituted with one, two, three, four or five substituents each independently selected from halo, $C_{1-6}$alkyl, $C_{3-7}$cycloalkyl, $C_{1-6}$alkyloxy, cyano, nitro, poly-halo$C_{1-6}$alkyl and polyhalo$C_{1-6}$alkyloxy;

Het is an aliphatic or aromatic heterocyclic radical; said aliphatic heterocyclic radical is selected from pyrrolidinyl, piperidinyl, homopiperidinyl, piperazinyl, morpholinyl, tetrahydrofuranyl and tetrahydrothienyl wherein each of said aliphatic heterocyclic radical may optionally be substituted with an oxo group; and said aromatic heterocyclic radical is selected from pyrrolyl, furanyl, thienyl, pyridinyl, pyrimidinyl, pyrazinyl and pyridazinyl wherein each of said aromatic heterocyclic radical may optionally be substituted with hydroxy.

The compounds of formula (II) can be prepared according to the methods described in the U.S. patent applications with application No. 60/143,962 and 60/107,792.

(III) is an antiviral compound of formula

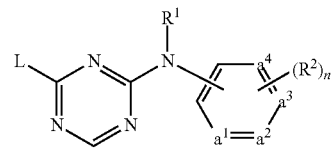

(III)

a N-oxide, a pharmaceutically acceptable addition salt, a quaternary amine or a stereochemically isomeric form thereof, wherein -a$^1$=a$^2$-a$^3$=a$^4$- represents a bivalent radical of formula —CH=CH—CH=CH— (a-1);

—N=CH—CH=CH— (a-2);

—N=CH—N=CH— (a-3);

—N=CH—CH=N— (a-4);

—N=N—CH=CH— (a-5);

n is 0, 1, 2, 3 or 4; and in case -a$^1$=a$^2$-a$^3$=a$^4$- is (a-1), then n may also be 5;

$R^1$ is hydrogen, aryl, formyl, $C_{1-6}$alkylcarbonyl, $C_{1-6}$alkyloxycarbonyl, $C_{1-6}$alkyl substituted with formyl, $C_{1-6}$alkylcarbonyl, $C_{1-6}$alkyloxycarbonyl; and each $R^2$ independently is hydroxy, halo, $C_{1-6}$alkyl optionally substituted with cyano or —C(=O)R$^4$, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, —S(=O)$_p$R$^4$, —NH—S(=O)$_p$R$^4$, —C(=O)R$^4$, —NHC(=O)H, —C(=O)NHNH$_2$, —NHC(=O)R$^4$, —C(=NH)R$^4$ or a radical of formula

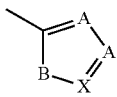

(c)

wherein each A independently is N, CH or CR$^4$;
B is NH, O, S or NR$^4$;
p is 1 or 2; and
R$^4$ is methyl, amino, mono- or dimethylamino or polyhalomethyl;
L is $C_{4-10}$alkyl, $C_{2-10}$alkenyl, $C_{2-10}$alkynyl, $C_{3-7}$cycloalkyl, whereby each of said aliphatic group may be substituted with one or two substituents independently selected from $C_{3-7}$cycloalkyl,
  indolyl or isoindolyl, each optionally substituted with one, two, three or four substituents each independently selected from halo, $C_{1-6}$alkyl, hydroxy, $C_{1-6}$alkyloxy, cyano, aminocarbonyl, nitro, amino, polyhalomethyl, poly-halomethyloxy and $C_{1-6}$alkylcarbonyl,
  phenyl, pyridinyl, pyrimidinyl, pyrazinyl or pyridazinyl, wherein each of said aromatic rings may optionally be substituted with one, two, three, four or five substituents each independently selected from the substituents defined in R$^2$; or
L is —X—R$^3$ wherein
  R$^3$ is phenyl, pyridinyl, pyrimidinyl, pyrazinyl or pyridazinyl, wherein each of said aromatic rings may optionally be substituted with two, three, four or five substituents each independently selected from the substituents defined in R$^2$; and
  X is —NR$^1$—, —NH—NH—, —N=N—, —O—, —C(=O)—, —CHOH—, —S—, —S(=O)— or —S(=O)$_2$—;
aryl is phenyl or phenyl substituted with one, two, three, four or five substituents each independently selected from halo, $C_{1-6}$alkyl, $C_{3-7}$cycloalkyl, $C_{1-6}$alkyloxy, cyano, nitro, polyhalo$C_{1-6}$alkyl and polyhalo$C_{1-6}$alkyloxy.

The compounds of formula (III) can be prepared according to the methods described in the U.S. patent application with application No. 60/107,799.

(IV) is an antiviral compound of formula

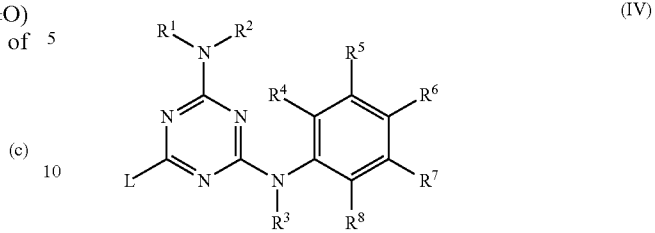

the pharmaceutically acceptable acid addition salts and the stereochemically isomeric forms thereof, wherein
R$^1$ and R$^2$ are each independently selected from hydrogen; hydroxy; amino; $C_{1-6}$alkyl; $C_{1-6}$alkyloxy; $C_{1-6}$alkylcarbonyl; $C_{1-6}$alkyl-oxycarbonyl; Ar$^1$; mono- or di($C_{1-6}$alkyl)amino; mono- or di($C_{1-6}$alkyl)aminocarbonyl; dihydro-2(3H)-furanone; $C_{1-6}$alkyl substituted with one or two substituents each independently selected from amino, imino, aminocarbonyl, aminocarbonyl-amino, hydroxy, hydroxy$C_{1-6}$alkyloxy, carboxyl, mono- or di($C_{1-6}$alkyl)amino, $C_{1-6}$alkyloxycarbonyl and thienyl; or
R$^1$ and R$^2$ taken together may form pyrrolidinyl, piperidinyl, morpholinyl, azido or mono- or di($C_{1-6}$alkyl)amino$C_{1-4}$-alkylidene;
R$^3$ is hydrogen, Ar$^1$, $C_{1-6}$alkylcarbonyl, $C_{1-6}$ alkyl, $C_{1-6}$alkyloxy-carbonyl, $C_{1-6}$alkyl substituted with $C_{1-6}$alkyloxycarbonyl; and
R$^4$, R$^5$, R$^6$, R$^7$ and R$^8$ are each independently selected from hydrogen, hydroxy, halo, $C_{1-6}$alkyl, $C_{1-6}$alkyloxy, cyano, amino-carbonyl, nitro, amino, trihalomethyl or trihalomethyloxy
L is $C_{1-10}$alkyl; $C_{3-10}$alkenyl; $C_{3-10}$alkynyl; $C_{3-7}$cycloalkyl; or
L is $C_{1-10}$alkyl substituted with one or two substituents independently selected from $C_{3-7}$cycloalkyl; indolyl or indolyl substituted with one, two, three or four substituents each independently selected from halo, $C_{1-6}$alkyl, cyano, aminocarbonyl, nitro, amino, trihalomethyl, trihalo-methyloxy, $C_{1-6}$alkylcarbonyl; phenyl or phenyl substituted with one, two, three, four or five substituents each independently selected from halo, hydroxy, $C_{1-6}$alkyloxy, cyano, aminocarbonyl, nitro, amino, trihalomethyl, trihalo-methyloxy, $C_{1-6}$alkylcarbonyl; and,
Ar$^1$ is phenyl, or phenyl substituted with one, two or three substituents each independently selected from halo, $C_{1-6}$alkyl, cyano, nitro or trifluoromethyl; with the proviso that compounds (a) to (o)

| Co. No. | Alk | R$^1$/R$^2$ | R$^3$ | R$^4$ | R$^5$ | R$^6$ | R$^7$ | R$^8$ |
| --- | --- | --- | --- | --- | --- | --- | --- | --- |
| a | 1-(4-(2-methylpropyl)phenyl)ethyl | H/H | H | CH$_3$ | H | H | H | H |
| b | 1-(4-(2-methylpropyl)phenyl)ethyl | H/H | H | H | H | NO$_2$ | H | H |
| c | 1-(4-(2-methylpropyl)phenyl)ethyl | H/H | C$_6$H$_5$ | H | H | H | H | H |
| d | 1-(4-(2-methylpropyl)phenyl)ethyl | H/H | H | NO$_2$ | H | CH$_3$ | H | H |
| e | 1-(4-(2-methylpropyl)phenyl)ethyl | H/H | H | H | H | NH$_2$ | H | H |
| f | 4-(2-methylpropyl)phenylmethyl | H/H | H | H | CF$_3$ | H | H | H |
| g | 1-(4-(2-methylpropyl)phenyl)ethyl | H/H | H | H | H | Cl | H | H |
| h | 4-(2-methylpropyl)phenylmethyl | H/H | H | H | H | H | H | H |
| i | 3,4-dimethoxyphenylmethyl | H/H | H | H | H | H | H | H |
| j | 2,3-dimethoxyphenylmethyl | H/H | H | H | H | H | H | H |
| k | 3,4-diethoxyphenylmethyl | H/H | H | H | H | H | H | H |
| l | 2-(3,5-(1,1-dimethylethyl)-4-hydroxy-phenyl)ethyl | H/H | H | H | H | H | H | H |

-continued

| Co. No. | Alk | $R^1/R^2$ | $R^3$ | $R^4$ | $R^5$ | $R^6$ | $R^7$ | $R^8$ |
|---|---|---|---|---|---|---|---|---|
| m | 2-(3,5-(1,1-dimethylethyl)-4-hydroxy-phenyl)ethyl | H/H | H | H | t-Bu | OH | t-Bu | H |
| n | Phenylmethyl | H/H | H | $CH_3$ | H | H | H | H |
| o | Phenylmethyl | H/H | H | H | H | H | H | H | are not included.

The compounds of formula (IV) can be prepared according to the methods described in EP-A-0834507.

(V) is an antifungal compound of formula

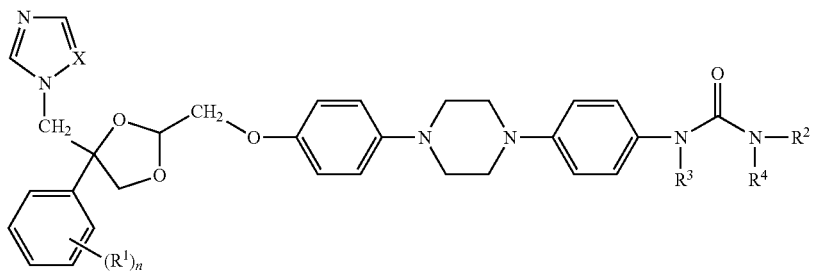

the N-oxide forms, the pharmaceutically acceptable acid addition salts and stereochemically isomeric forms thereof, wherein n is zero, 1, 2 or 3;

X is N or CH;

each $R^1$ independently is halo, nitro, cyano, amino, hydroxy, $C_{1-4}$alkyl, $C_{1-4}$alkyloxy or trifluoromethyl;

$R^2$ is hydrogen; $C_{3-7}$alkenyl; $C_{3-7}$alkynyl, aryl; $C_{3-7}$cycloalkyl; $C_{1-6}$alkyl or $C_{1-6}$alkyl substituted with hydroxy, $C_{1-4}$alkyloxy, $C_{3-7}$cycloalkyl or aryl;

$R^3$ and $R^4$ each independently are hydrogen, $C_{1-6}$alkyl, $C_{3-7}$cyclo-alkyl or aryl; or $R^3$ and $R^4$ taken together form a bivalent radical $-R^3-R^4-$ of formula:

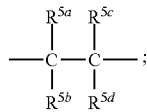 (a)

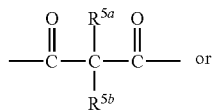 (b)

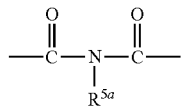 (c)

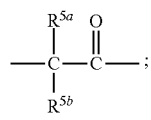 (d)

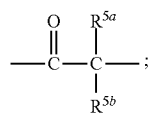 (e)

wherein $R^{5a}$, $R^{5b}$, $R^{5c}$, $R^{5d}$ each independently are hydrogen, $C_{1-6}$alkyl or aryl; and aryl is phenyl or phenyl substituted with one, two or three substituents selected from halo, nitro, cyano, amino, hydroxy, $C_{1-4}$alkyl, $C_{1-4}$alkyloxy or trifluoromethyl.

The compounds of formula (V) can be prepared according to the methods described in WO 99/02523.

(VI) is an apolipoprotein-B synthesis inhibitor of formula

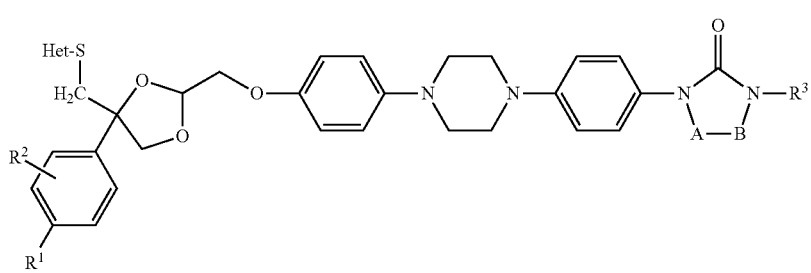

the N-oxides, the stereochemically isomeric forms thereof, and the pharmaceutically acceptable acid addition salts, wherein A and B taken together form a bivalent radical of formula:

—N=CH— (a),

—CH=N— (b),

—CH₂—CH₂— (c),

—CH=CH— (d),

—C(=O)—CH₂— (e),

—CH₂—C(=O)— (f), in the bivalent radicals of formula (a) and (b) the hydrogen atom may be replaced by $C_{1-6}$alkyl; in the bivalent radicals of formula (c), (d), (e), (f), one or two hydrogen atoms may be replaced by $C_{1-6}$alkyl;
$R^1$ is hydrogen, $C_{1-6}$alkyl or halo;
$R^2$ is hydrogen or halo;
$R^3$ is hydrogen; $C_{1-8}$alkyl; $C_{3-6}$cycloalkyl; or $C_{1-8}$alkyl substituted with hydroxy, oxo, $C_{3-6}$cycloalkyl or aryl;
Het is a heterocycle selected from the group consisting of pyridine; pyridine substituted with one or two substituents selected from $C_{1-6}$alkyl, hydroxy, trihalomethyl, amino, mono- or di($C_{1-6}$alkyl)amino or aryl; pyrimidine; pyrimidine substituted with one or two substituents selected from $C_{1-6}$alkyl, hydroxy, trihalomethyl, amino, mono- or di($C_{1-6}$alkyl)-amino or aryl; tetrazole; tetrazole substituted with $C_{1-6}$alkyl or aryl; triazole; triazole substituted with one or two substituents selected from $C_{1-6}$alkyl, hydroxy, $C_{1-6}$alkyloxy, trihalomethyl, amino, mono- or di($C_{1-6}$lkyl)-amino; thiadiazole; thiadiazole substituted with one or two substituents selected from $C_{1-6}$alkyl, hydroxy, trihalomethyl, amino, mono- or di($C_{1-6}$alkyl)-amino; oxadiazole substituted with one or two substituents selected from $C_{1-6}$alkyl, hydroxy, trihalomethyl, amino, mono- or di($C_{1-6}$alkyl)amino; imidazole; imidazole substituted with one or two substituents selected from $C_{1-6}$alkyl, hydroxy, trihalomethyl, amino, mono- or di($C_{1-6}$alkyl)amino; thiazole; thiazole substituted with one or two substituents selected from $C_{1-6}$alkyl, hydroxy, trihalomethyl, amino, mono- or di($C_{1-6}$alkyl)amino; oxazole; oxazole substituted with one or two substituents selected from $C_{1-6}$alkyl, hydroxy, trihalomethyl, amino, mono- or di($C_{1-6}$alkyl)amino;
aryl is phenyl or phenyl substituted with $C_{1-6}$alkyl or halo.

The heterocyclic radical "Het" is bound to the sulfur atom via a carbon atom.

The compounds of formula (VI) can be prepared according to the methods described in WO 96/13499.

The particles comprise the compounds of formula (I) to (VI) as a solid dispersion in a polymeric matrix, wherein the poly-meric matrix is consisting of a homo- or copolymer of N-vinyl-pyrrolidone. Furthermore, the invention concerns a process for manufacturing of such particles and pharmaceutical dosage forms comprising such particles.

The compounds of formula (I) to (VI) contained in the particles show poor bio-availability.

In order to improve the dissolution characteristics the compounds are dispersed in a polymeric matrix, preferably by using a melt-extrusion process.

EP-A 0 240 904 discloses a method for producing solid pharmaceutical forms by extrusion of polymer melts which contain active substances, using as polymers homo- or copolymers of N-vinyl-pyrrolidone.

EP-B 0 580 860 discloses a method for producing solid dispersions of drug substances in a polymeric matrix using a twin screw extruder.

It is an object of the present invention to provide rate-controlled pharmaceutical forms containing the aforementioned compounds.

We have found that this object is achieved by the particles defined at the outset.

Preferred compounds according to the invention are:
4-[[4-[(2,4,6-trimethylphenyl)amino]-2-pyrimidinyl]amino]benzo-nitrile;
4-[[2-[(cyanophenyl)amino]-4-pyrimidinyl]amino]-3,5-dimethyl-benzonitrile;
4-[[4-amino-5-chloro-6-[(2,4,6-trimethylphenyl)amino]-2-pyrimidinyl]-amino]benzonitrile;
4-[[5-chloro-4-[(2,4,6-trimethylphenyl)amino]-2-pyrimidinyl]-amino]benzonitrile;
4-[[5-bromo-4-(4-cyano-2,6-dimethylphenoxy)-2-pyrimidinyl]-amino]benzonitrile;
4-[[4-amino-5-chloro-6-[(4-cyano-2,6-dimethylphenyl)amino]-2-pyrimidinyl]amino]benzonitrile;
4-[[5-bromo-6-[(4-cyano-2,6-dimethylphenyl)amino]-2-pyrimidinyl]-amino]benzonitrile;
4-[[4-amino-5-chloro-6-(4-cyano-2,6-dimethylphenyloxy)-2-pyrimidinyl]amino]benzonitrile;
4-[[4-amino-5-bromo-6-(4-cyano-2,6-dimethylphenyloxy)-2-pyrimidinyl]amino]benzonitrile;
4-[[4-[(2,4,6-trimethylphenyl)amino]-1,3,5-triazin-2-yl]amino]-benzonitrile;
4-[[4-amino-6-[(2,6-dichlorophenyl)methyl]-1,3,5-triazin-2-yl]-amino]benzonitrile;
4-[[4-[(2,6-dichlorophenyl)methyl]-6-(hydroxyamino)-1,3,5-triazin-2-yl]amino]benzonitrile;
1-[4-[4-[4-[[4-(2,4-difluorophenyl)-4-(1H-1,2,4-triazol-1-yl-methyl)-1,3-dioxolan-2-yl]methoxy]phenyl]-1-piperazinyl]phenyl]-3-(1-methylethyl)-2-imidazolidinone;
(−)-[2S-[2alpha,4alpha(S*)]]-4-[4-[4-[4-[[2-(4-chlorophenyl)-2-[[(4-methyl-4H-1,2,4-triazol-3-yl)thio]methyl]-1,3-dioxolan-4-yl]methoxy]phenyl]-1-piperazinyl]phenyl]-2,4-dihydro-2-(1-methyl-propyl)-3H-1,2,4-triazol-3-one,
a N-oxide, a pharmaceutically acceptable addition salt or a stereochemically isomeric form thereof.

According to the present invention the term "rate-controlled" means that depending on the composition of the matrix the particles can show instant release of the active ingredient or modified release (sustained release).

The compounds according to the invention are homogeneously dispersed in a polymer matrix consisting of a homopolymer of N-vinylpyrrolidone or, preferably, a copolymer of N-vinyl-pyrrolidone. A preferred copolymer is a copolymer of N-vinyl-pyrrolidone and vinyl acetate, especially a copolymer obtained from 60% b.w. of NVP and 40% b.w. of vinylacetate.

The polymers show Fikentscher K values of from 17 to 90, preferably a K value of 30 (for the definition of the K value see "H. Fikentscher, Cellulose-Chemie" (1932), 58-64 and 71-74).

The polymeric matrix component is used in amounts of from 40 to 70, preferably of from 50 to 65% b.w. of the total weight of the particles.

In a preferred embodiment of the invention the polymeric matrix further comprises a surfactant, preferably a surfactant with a HLB-value of 10-18 (HLB: Hydrophilic Lipophilic Balance). Especially preferred surfactants are selected form the group consisting of low molecular weight polyoxyethylene polyoxy-propylene block copolymers with a mean molecular weight of 1000 to 6000 g/mol, and hydrogenated castor oil which can be modified with polyethylene glycol.

The amounts of surfactants used lies in the range of up to 20% b.w., preferably 5 to 15% b.w., of the particles.

In another preferred embodiment the matrix further comprises an organic carboxylic acid in amounts of up to 5% b.w. of the particles.

In another preferred embodiment of the invention the polymeric matrix further comprises hydroxypropyl methyl cellulose in amounts of up to 25% b.w., preferably from 5 to 10% b.w.

The particles of the present invention are prepared as solid dispersions of the active compounds in a polymeric matrix. The term "solid dispersion" is well known in the art and means a dispersion consisting of solid components. Preferably solid dispersions are in the form of solid solutions wherein the active ingredients are molecularly dispersed in the polymeric matrix.

Such solid dispersion is preferably obtained by forming a homogeneous mixture of the components in the form of a melt, extruding said melt and shaping of the extrudate. The melting is effected by the input of thermal and/or mechanic energy. Depending on the composition of the matrix, the melting takes place in the range of from 40° C. to 190° C., preferably 50 to 150° C.

The suitable temperature range depends on the glass transition temperature of the polymer component, the properties of the active ingredients and further additives. The optimal temperature range can be established by a few simple tests.

The mixing of the active substances with the polymer and additional components of the matrix can take place before or after the melting of the polymer. Preferably the process is solvent-free which means that no additional organic solvents or water are added.

The plastification and melting preferably can take place in an extruder, a kneader or a mixing reactor, preferably in an extruder having one or more screws which may rotate in the same direction or opposite directions, especially in a twin screw extruder. The latter can be operated with or without kneading elements, but use of kneading elements is preferred because mixing is better.

The still plastic material is extruded through a die or a breaker plate and then shaped into particles. This may be effected by milling and subsequent sieving the cooled extrudate. The preferred particle size for instant release forms lies in the range of from 0.5 to 1.5 mm.

The particles, optionally together with conventional pharmaceutically acceptable excipients, may be further processed to conventional pharmaceutical dosage forms such as tablets, pastilles, suppositories, or be packed in capsules.

It is possible and particularly advantageous to produce pharmaceutical forms with rate-controlled release and improved dissolution rates of the active ingredients. This was not to be expected in view of the low solubility of the active ingredients in aqueous media.

EXAMPLES

General Method

Powder mixes of the components were melt kneaded at 145° C. for 5 min. After cooling the solidified melts were ground and sieved. The sieve fraction 0.5-1.5 mm was used for the dissolution tests.

The composition of the individual powder mixes is listed in Table 1.

TABLE 1

| Example No. | 1 | 2 | 3 | 4 | 5 | 6 |
|---|---|---|---|---|---|---|
| Active ingredient[1] | 30 | 30 | 30 | 30 | 30 | 40 |
| VP-VAC-copolymer[2] | 65 | 55 | 55 | 60 | 55 | 47.1 |
| Surfactant[3] | 5 | 15 |  |  | 5 | 4.3 |
| Citric acid |  |  |  | 5 |  |  |
| HPMC |  |  |  |  | 10 | 8.6 |
| Surfactant[4] |  |  | 15 |  |  |  |

[1] 4-[[4-[2,4,6-trimethylphenyl)amino]-2-pyrimidinyl]amino]-benzonitrile
[2] Kollidon ® VA64, VP/VAC = 60/40, BASF Aktiengesellschaft
[3] PEG-n-hydrogenated Castoroil
[4] polyoxyethylene polyoxypropylene blockcopolymer, mean mol. weight 4000 g/mol The dissolution tests were carried out according to USP XXIII, paddle model, pH no change test, 0.1 M HCl, at 37° C., 100 rpm The results are listed in Table 2.

TABLE 2

Dissolution Rates of particles according to examples 1-6

| | Dissolution [%] | | | | | Dissolution [%] | |
|---|---|---|---|---|---|---|---|
| time [min] | Ex. 1 (IR) | Ex. 2 (IR) | Ex. 3 (IR) | Ex. 4 (IR) | time [min] | Ex. 5 (SR) | Ex. 6 (SR) |
| 5 | 53 | 65 | 58 | 57 | 1 | | |
| 10 | 73 | 86 | 88 | 82 | 2 | | |
| 15 | 77 | 91 | 95 | 89 | 3 | | |
| 20 | 81 | 91 | 96 | 93 | 4 | | |
| 30 | 87 | 94 | 99 | 94 | 6 | | |
| 60 | 92 | 93 | 96 | 94 | 8 | 96 | 95 |
| 120 | 93 | 94 | 97 | 95 | | | |
| | IR: Instant Release | | | | | SR: Sustained Release | |

DSC-Measurements were performed with the formulations according to examples 1 to 6 in open pans (air) at temperatures of from 20→250° C., with a heating rate of 10° C. per minute. There is no indication of crystalline drug substance in the solid dispersions.

The invention claimed is:

1. Rate-controlled release particles, comprising a compound of formula II $$\text{(II)}$$

an N-oxide, a pharmaceutically acceptable addition salt, a quaternary amine or a stereochemically isomeric form thereof, wherein $-b^1=b^2-C(R^{2a})=b^3-b^4=$ represents a bivalent radical of formula $$-CH=CH-C(R^{2a})=CH-CH= \quad \text{(b-1)};$$

$$-N=CH-C(R^{2a})=CH-CH= \quad \text{(b-2)};$$

$$-CH=N-C(R^{2a})=CH-CH= \quad \text{(b-3)};$$

$$-N=CH-C(R^{2a})=N-CH= \quad \text{(b-4)};$$

—N=CH—C(R$^{2a}$)=CH—N=   (b-5);

—CH=N—C(R$^{2a}$)=N—CH=   (b-6);

—N=N—C(R$^{2a}$)=CH—CH=   (b-7);

q is 0, 1, 2; or where possible q is 3 or 4;
R$^l$ is hydrogen, aryl, formyl, C$_{1-6}$alkylcarbonyl, C$_{1-6}$alkyl, C$_{1-6}$alkyloxycarbonyl, C$_{1-6}$alkyl substituted with formyl, C$_{1-6}$alkylcarbonyl, C$_{1-6}$alkyloxycarbonyl;
R$^{2a}$ is cyano, aminocarbonyl, mono- or di(methyl)aminocarbonyl, C$_{1-6}$alkyl substituted with cyano, aminocarbonyl or mono- or di(methyl)aminocarbonyl, C$_{2-6}$alkenyl substituted with cyano, or C$_{2-6}$alkynyl substituted with cyano;
each R$^2$ independently is hydroxy, halo, C$_{1-6}$alkyl optionally substituted with cyano or —C(=O)R$^6$, C$_{3-7}$cycloalkyl, C$_{2-6}$alkenyl optionally substituted with one or more halogen atoms or cyano, C$_{2-6}$alkynyl optionally substituted with one or more halogen atoms or cyano, C$_{1-6}$alkyloxy, C$_{1-6}$alkyloxycarbonyl, carboxyl, cyano, nitro, amino, mono- or di(C$_{1-6}$alkyl)amino, polyhalomethyl, polyhalomethyloxy, polyhalomethylthio, —S(=O)OR$^6$, —NH—S(=O)$_p$R$^6$, —C(=O)R$^6$, —NHC(=O)H, —C(=O)NHNH$_2$, —NHC(=O)R$^6$, —C(=NH)R$^6$ or a radical of formula

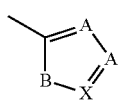   (c)

wherein each A independently is N, CH or CR$^6$;
B is NH, O, S or NR$^6$;
p is 1 or 2; and
R$^6$ is methyl, amino, mono- or dimethylamino or polyhalomethyl;
L is C$_{1-10}$alkyl, C$_{2-10}$alkenyl, C$_{2-10}$alkynyl, C$_{3-7}$cycloalkyl, whereby each of said aliphatic group may be substituted with one or two substituents independently selected from
  C$_{3-7}$cycloalkyl,
  indolyl or isoindolyl, each optionally substituted with one, two, three or four substituents each independently selected from halo, C$_{1-6}$alkyl, hydroxy, C$_{1-6}$alkyloxy, cyano, aminocarbonyl, nitro, amino, polyhalomethyl, polyhalomethyloxy and C$_{1-6}$alkylcarbonyl,
  phenyl, pyridinyl, pyrimidinyl, pyrazinyl or pyridazinyl, wherein each of said aromatic rings may optionally be substituted with one, two, three, four or five substituents each independently selected from the substituents defined in R$^2$; or
L is —X—R$^3$ wherein
  R$^3$ is phenyl, pyridinyl, pyrimidinyl, pyrazinyl or pyridazinyl, wherein each of said aromatic rings may optionally be substituted with one, two, three, four or five substituents each independently selected from the substituents defined in R$^2$; and
  X is —NH—, —NH—NH—, —N=N—, —O—, —C(=O)—, —CHOH—, —S—, —S(=O)— or —S(=O)$_2$—;
Q represents hydrogen, C$_{1-6}$alkyl, halo, polyhaloC$_{1-6}$alkyl or —NR$^4$R$^5$; and
R$^4$ and R$^5$ are each independently selected from hydrogen, hydroxy, C$_{1-12}$alkyl, C$_{1-12}$alkyloxy, C$_{1-12}$alkylcarbonyl, C$_{1-12}$alkyloxycarbonyl, aryl, amino, mono- or di(C$_{1-12}$alkyl)amino, mono- or di(C$_{1-12}$alkyl)aminocarbonyl
  wherein each of the aforementioned C$_{1-12}$alkyl groups may optionally and each individually be substituted with one or two substituents each independently selected from hydroxy, C$_{1-6}$alkyloxy, hydroxyc$_{1-6}$alkyloxy, carboxyl, C$_{1-6}$alkyloxycarbonyl, cyano, amino, imino, mono- or di(C$_{1-6}$alkyl)amino, polyhalomethyl, polyhalomethyloxy, polyhalomethylthio, —S(O)$_p$R$^6$, —NH—S(=O)$_p$R$^6$, —C(=O)R$^6$, —NHC(=O)H, —C(=O)NHNH$_2$, —NHC(O)R$^6$, —C(=NH)R$^6$, aryl and Het; or
R$^4$ and R$^5$ taken together may form pyrrolidinyl, piperidinyl, morpholinyl, azido or mono- or di(C$_{1-12}$alkyl)aminoC$_{1-4}$-alkylidene;
Y represents hydroxy, halo, C$_{3-7}$cycloalkyl, C$_{2-6}$alkenyl optionally substituted with one or more halogen atoms, C$_{2-6}$alkynyl optionally substituted with one or more halogen atoms, C$_{1-6}$alkyl substituted with cyano or —C(=O)R$^6$, C$_{1-6}$alkyloxy, C$_{1-6}$alkyloxycarbonyl, carboxyl, cyano, nitro, amino, mono- or di(C$_{1-6}$alkyl)amino, polyhalomethyl, polyhalomethyloxy, polyhalomethylthio, —S(=O)$_p$R$^6$, —NH—S(=O)$_p$R$^6$, —C(=O)R$^6$, —NHC(=O)H, —C(=O)NHNH$_2$, —NHC(=O)R$^6$, —C(NH)R$^6$ or aryl;
aryl is phenyl or phenyl substituted with one, two, three, four or five substituents each independently selected from halo, C$_{1-6}$alkyl, C$_{3-7}$cycloalkyl, C$_{1-6}$alkyloxy, cyano, nitro, polyhaloC$_{1-6}$alkyl and polyhaloC$_{1-6}$alkyloxy;
Het is an aliphatic or aromatic heterocyclic radical;
  said aliphatic heterocyclic radical is selected from pyrrolidinyl, piperidinyl, homopiperidinyl, piperazinyl, morpholinyl, tetrahydrofuranyl and tetrahydrothienyl wherein each of said aliphatic heterocyclic radical may optionally be substituted with an oxo group; and said aromatic heterocyclic radical is selected from pyrrolyl, furanyl, thienyl, pyridinyl, pyrimidinyl, pyrazinyl and pyridazinyl wherein each of said aromatic heterocyclic radical may optionally be substituted with hydroxy,
as a solid dispersion in a polymeric matrix, wherein the polymeric matrix is consisting of a copolymer of N-vinylpyrrolidone with vinyl acetate.

2. Particles according to claim 1, wherein the compound of formula (II) is molecularly dispersed in the polymeric matrix.

3. Particles according to claim 1, further comprising a surfactant.

4. Particles according to claim 3, wherein the surfactant is a PEG-n-hydrogenated castor oil.

5. Particles according to claim 1, wherein the surfactant is a low molecular weight polyoxyethylene polyoxypropylene block copolymer.

6. Particles according to claim 1, further comprising citric acid in amounts of up to 5% b.w.

7. Particles according to claim 1, wherein the copolymer of N-vinylpyrrolidone is used in amounts of from 40 to 70% b.w. of the total weight of the dosage form.

8. Particles according to claim 7, wherein the copolymer of N-vinylpyrrolidone is used in amounts of from 50 to 65% b.w.

9. Particles according to claim 1, wherein the controlled release is an instant release of the drug.

10. Particles according to claim 1, wherein the controlled release is a sustained release.

11. Particles according to claim 10, further comprising hydroxypropyl methyl cellulose in amounts of from 5 to 10% b.w.

12. Particles according to claim 1, obtained by forming a homogeneous mixture of the components in the form of a melt, extruding said mixture and shaping of the extrudate.

13. Particles according to claim 1, comprising a compound selected from the group consisting of
- 4- [[4-amino-5-chloro-6-[(2,4,6-trimethylphenyl)amino]-2-pyrimidinyl]-amino]benzonitrile;
- 4- [[5-chloro-4-[(2,4,6-trimethylphenyl)amino]-2-pyrimidinyl]amino]benzonitrile;
- 4-[[5-bromo-4-(4-cyano-2,6-dimethylphenoxy)-2-pyrimidin]amino]-benzonitrile;
- 4-[[4-amino-5-chloro-6-[(4-cyano-2,6-dimethylphenyl)amino]-2-pyrimidinyl]amino]benzonitrile;
- 4-[[5-bromo-6-[(4-cyano-2,6-dimethylphenyl)amino]-2-pyrimidinyl]-amino]benzonitrile;
- 4-[[4-amino-5-chloro-6-[(4-cyano-2,6-dimethylphenoxy)-2-pyrimi-dinyl]amino]benzonitrile;
- 4-[[4-amino-5-bromo-6-(4-cyano-2,6-dimethylphenyloxy)-2-pyrimi-dinyl]amino]benzonitrile;
- a N-oxide, a pharmaceutically acceptable addition salt or a stereochemically isomeric form thereof.

14. Pharmaceutical dosage form, comprising particles according to claim 1.

15. Pharmaceutical dosage forms according to claim 14, further comprising one or more pharmaceutically acceptable excipients.

16. Pharmaceutical dosage forms according to claim 14 comprising particles wherein the compound of formula (II) is molecularly dispersed in the polymeric matrix.

\* \* \* \* \*